United States Patent
Persson et al.

(10) Patent No.: US 11,273,084 B2
(45) Date of Patent: Mar. 15, 2022

(54) ABSORBENT ARTICLE WITH BREATHABLE BACKSHEET

(71) Applicant: Essity Hygiene and Health Aktiebolag, Gothenburg (SE)

(72) Inventors: Ulrika Persson, Gothenburg (SE); Pia Kalentun, Gothenburg (SE); Ida Jensen, Gothenburg (SE)

(73) Assignee: Essity Hygiene and Health Aktiebolag, Gothenburg (SE)

(*) Notice: Subject to any disclaimer, the term of this patent is extended or adjusted under 35 U.S.C. 154(b) by 532 days.

(21) Appl. No.: 16/321,725

(22) PCT Filed: Aug. 24, 2016

(86) PCT No.: PCT/SE2016/050793
§ 371 (c)(1),
(2) Date: Jan. 29, 2019

(87) PCT Pub. No.: WO2018/038656
PCT Pub. Date: Mar. 1, 2018

(65) Prior Publication Data
US 2020/0107974 A1 Apr. 9, 2020

(51) Int. Cl.
*A61F 13/514* (2006.01)
*A61F 13/472* (2006.01)
(Continued)

(52) U.S. Cl.
CPC ...... *A61F 13/51458* (2013.01); *A61F 13/472* (2013.01); *A61F 13/535* (2013.01);
(Continued)

(58) Field of Classification Search
CPC ............ A61F 13/51458; A61F 13/5146; A61F 13/51462; A61F 13/5605; A61F 13/5611;
(Continued)

(56) References Cited

U.S. PATENT DOCUMENTS 4,186,743 A   2/1980  Steiger
4,554,191 A  11/1985  Korpman
(Continued)

FOREIGN PATENT DOCUMENTS

CN  87104852 A   2/1988
CN   1222068 A   7/1999
(Continued)

OTHER PUBLICATIONS

Colombian Patent Office, Office Action 9434, Colombian Application No. NC2019/0001554, dated Aug. 4, 2020 (18 pages).
(Continued)

*Primary Examiner* — Catharine L Anderson
(74) *Attorney, Agent, or Firm* — Wood Herron & Evans LLP (57) ABSTRACT

The present invention relates to an absorbent article comprising a liquid permeable topsheet, a liquid-impermeable backsheet and an absorbent core positioned between the topsheet and the backsheet. The absorbent article comprises pressure sensitive adhesive on a garment facing surface of the backsheet, and the backsheet is a breathable polyolefin-based film and has a Water Vapour Transmission Rate measured according to NWSP 070.4.RO (15) of at least 1000 g/m²/24 h, preferably at least 3000 g/m²/24 h, and a tear resistance measured according to Elmendorf Tear ASTM D1922 (15) of at least 300 mN.

19 Claims, 6 Drawing Sheets

US 11,273,084 B2
Page 2

(51) Int. Cl.
*A61F 13/535* (2006.01)
*A61F 13/56* (2006.01)
*A61L 15/18* (2006.01)
*B32B 27/32* (2006.01)

(52) U.S. Cl.
CPC .......... *A61F 13/5616* (2013.01); *A61L 15/18* (2013.01); *A61F 2013/51409* (2013.01); *B32B 27/32* (2013.01)

(58) Field of Classification Search
CPC .......... A61F 13/476; A61F 2013/51409; A61F 2013/51411; A61F 2013/51413; A61F 2013/51417; A61F 2013/51419
See application file for complete search history.

(56) References Cited

U.S. PATENT DOCUMENTS

| | | | |
|---|---|---|---|
| 5,126,391 A * | 6/1992 | Yamamoto | C08K 3/013 524/310 |
| 5,785,699 A | 7/1998 | Schmitz | |
| 6,096,014 A | 8/2000 | Haffner et al. | |
| 8,029,487 B2 | 10/2011 | Bagger-Sjöbäck et al. | |
| 9,066,837 B2 | 6/2015 | Kim et al. | |
| 2001/0041487 A1 | 11/2001 | Brady et al. | |
| 2005/0203478 A1* | 9/2005 | Veglio | A61L 15/42 604/387 |
| 2006/0014897 A1* | 1/2006 | Myhre | C08L 23/06 525/89 |
| 2007/0155900 A1* | 7/2007 | Chang | C08L 53/025 525/88 |
| 2009/0036856 A1* | 2/2009 | Woltman | A61F 13/15 604/385.01 |
| 2010/0121295 A1* | 5/2010 | Collias | A61F 13/49014 604/367 |
| 2013/0184664 A1 | 7/2013 | Matsushima et al. | |
| 2016/0166447 A1 | 6/2016 | Toro et al. | |
| 2017/0008211 A1* | 1/2017 | Middlesworth | B29C 48/914 |
| 2017/0152377 A1* | 6/2017 | Wang | B32B 27/32 |

FOREIGN PATENT DOCUMENTS

| | | |
|---|---|---|
| CN | 1258305 A | 6/2000 |
| CN | 1460058 A | 12/2003 |
| CN | 101902997 A | 12/2010 |
| EP | 0779325 A2 | 6/1997 |
| EP | 1152025 A1 | 11/2001 |
| EP | 1574226 A1 | 9/2005 |
| GB | 2068968 A | 8/1981 |
| JP | 3137604 B2 | 2/2001 |
| JP | 2004099665 A | 4/2004 |
| RU | 2426522 C2 | 8/2011 |
| RU | 2555661 C2 | 7/2015 |
| WO | 0020208 A1 | 4/2000 |
| WO | 0023509 A1 | 4/2000 |
| WO | 0037014 A1 | 6/2000 |
| WO | 0197738 A2 | 12/2001 |
| WO | 0226182 A2 | 4/2002 |
| WO | 2005087281 A1 | 9/2005 |
| WO | 2006071161 A1 | 7/2006 |
| WO | 2008060204 A1 | 5/2008 |
| WO | 2015175593 A1 | 11/2015 |

OTHER PUBLICATIONS

International Preliminary Report on Patentability for Application No. PCT/SE2016/050793, dated Nov. 15, 2018—7 pages.
International Search Report and Written Opinion for Application No. PCT/SE2016/050793, dated May 9, 2017—13 pages.
National Intellectual Property Administration (CNIPA) of the People's Republic of China, Notification of the First Office Action, Application No. 201680088088.4, dated Dec. 3, 2020 (18 pages).
Australian Examination Report for Australian Application No. 2016420321, dated Jun. 21, 2019, 3 pages.
Columbian Third Party Opposition for Columbian Application No. NC2019/0001554, dated Sep. 20, 2019 with translation, 19 pages.
Australian Examination Report for Australian Application No. 2016420321, dated Sep. 30, 2019, 5 pages.
Brazilian Patent and Trademark Office, Search Report and Written Opinion, Brazilian Application No. BR112018076381-0, dated May 18, 2020 (4 pages).
Russian Decision to Grant a Patent for Russian Application No. 2019108263/12(015896), dated Aug. 30, 2019 with translation, 15 pages.
Extended European Search Report for European Application No. 16 914 327.8, dated Feb. 20, 2020, 6 pages.
Australian Notice of Acceptance for Patent Application for Australian Application No. 2016420321, dated Jan. 15, 2020, 3 pages.
National Intellectual Property Administration (CNIPA) of the People's Republic of China, Notification of the 2nd Office Action, Application No. 201680088088.4, dated Aug. 11, 2021 with English Translation (17 pages).
Intellectual Property Corporation of Malaysia, Substantive Examination Adverse Report issued in application No. PI2019000793 dated Sep. 21, 2021, 3 pages.

\* cited by examiner

ABSORBENT ARTICLE WITH BREATHABLE BACKSHEET

CROSS REFERENCE TO RELATED APPLICATIONS

This is a U.S. National Phase application of PCT/SE2016/050793, filed Aug. 24, 2016, the disclosure of which is incorporated herein by reference in its entirety for all purposes.

TECHNICAL FIELD

The present invention relates to an absorbent article, such as an incontinence article, sanitary towel and panty liner, for personal hygiene use as defined in the appended claims.

BACKGROUND ART

Absorbent articles, such as incontinence articles, sanitary towels and panty liners, are disposable products for personal hygiene use and normally comprise a liquid-permeable topsheet, absorbent core and liquid-impermeable backsheet. The absorbent article is fastened on a garment of the user by means of adhesive or for example by means hook-and-loop materials. Absorbent articles require high comfort in use. Especially, it is important that the conditions of the microclimate between skin of the user and the absorbent article are satisfactory to perceive comfort. Occlusion of the skin leads to increased humidity which increases growth of microorganisms, enhances skin degradation, facilitates skin penetration of potentially toxic substances and increases the risk for chafing. Therefore, it is desirable that absorbent articles are breathable. To render the absorbent articles breathable, or to increase the breathability of absorbent articles, backsheet materials that are breathable while still liquid-impermeable, are commonly used in absorbent articles. Such backsheet materials are known in the art and are generally microporous and usually contain an inorganic filler material, such as calcium carbonate. However, inorganic fillers may weaken the backsheet materials, which is not desirable.

Use of hot-melt and emulsion-based adhesives to attach an absorbent article on a garment is well known in the art. Traditionally, cotton has been a common material for example in underwear on which the absorbent articles have been attached. Today however, synthetic fabric materials, such as micro-fibre fabrics e.g. polyester, are commonly used in the garments. Absorbent articles may be difficult to fasten to synthetic fabrics and the problem has been noted for example in WO2005087281.

Absorbent articles should nevertheless be attached on garments of the users so that they will sit well and be securely attached on all kinds of fabrics during the use of the article. However, it has been noted that while the absorbent articles are securely attached on the garments, they may become difficult to remove from the garments. Thus, considerable removal forces may be needed to remove the absorbent article from the garment. Breathable backsheet materials are desirable due to improved microclimate to the wearer, but they are weaker than non-breathable films. As mentioned above, this is due to the fact that breathable films contain up to 40-60% of an inorganic particulate filler material, such as calcium carbonate. Microporous films can be manufactured either by casting or blowing followed by stretching the film. When the film is stretched, cavities are formed around the particles. These cavities are large enough for moisture in gaseous phase to be transported through the film, but too small for liquid to pass through. Therefore, such film materials are breathable, but liquid-impermeable but also weaker than unbreathable films that do not contain an inorganic particulate filler material. Furthermore, since there is a desire to decrease material costs, the grammage of the backsheet films is decreased and the films become even more brittle and can thus easily break. Therefore, there may be a risk that the absorbent article breaks and pieces of the article will remain attached to the garment when product is removed from the underwear after use. Alternatively or additionally, there is a risk that adhesive residues will remain on the garment and these residues may be difficult to remove from the garment. Also, there is a risk that the garment will be damaged if substantial forces need to be used to remove the article from the garment of the user.

Thus, there is a need to provide an absorbent article which is breathable, which has a liquid-impermeable backsheet and which has an adequate strength so that the product may be removed from a garment after use such that the product and/or the garment are not damaged.

SUMMARY

In view of the above, the present invention includes an absorbent article for personal hygiene which is breathable, is securely attachable on a garment, especially on a garment comprising or consisting of synthetic fabric, while it can be removed from the garment without damaging the absorbent article or the garment.

It is a further objective to provide different types of breathable absorbent articles for personal hygiene which fulfil the objectives above.

It is also an objective to provide an absorbent article for personal hygiene with an adhesive coating which securely attaches the article on a garment while it can be easily removed from a garment after use.

Furthermore, it is an objective to provide an aesthetically pleasant product which can be easily manufactured in existing production machinery.

It is another object to provide an absorbent article with increased breathability with a backsheet material that contains a relatively high amount of inorganic filler while the backsheet material has a good tear resistance.

In the present disclosure a relation between the breathability and strength that is satisfactory has been found. The present invention thus relates to an absorbent article comprising a liquid-permeable topsheet having a body facing surface and a garment facing surface, a liquid-impermeable backsheet having a body facing surface and a garment facing surface, wherein an absorbent core is positioned between the topsheet and the backsheet, and wherein the absorbent article has a longitudinal central line extending through the absorbent article and wherein the absorbent article extends in the direction of the longitudinal central line and a transverse direction, which is perpendicular to the direction of the longitudinal central line, and the absorbent article further comprises pressure sensitive adhesive on the garment facing surface of the backsheet, and wherein the backsheet is a breathable polyolefin-based film and has a Water Vapour Transmission Rate measured according to NWSP 070.4.RO (15) of at least 1000 $g/m^2/24$ h, preferably at least 3000 $g/m^2/24$ h, and a tear resistance measured according to Elmendorf Tear ASTM D1922(15) of at least 300 mN.

The breathability and the tear resistance above have been found to provide an absorbent article for personal hygiene which is breathable, is securely attachable on a garment, especially on a garment comprising or consisting of synthetic fabric, while it can be removed from the garment without damaging the absorbent article or the garment.

The absorbent core can according to one variant have a smaller extension in a plane of the longitudinal and transverse extension of the backsheet and/or topsheet. The body facing surface of the backsheet can be joined to the garment facing surface of the topsheet. In this way an improved leakage control can be provided.

In another variant, the absorbent core, the backsheet and the topsheet can have substantially the same extension in a plane of the longitudinal and transverse extension of the absorbent article and wherein the edge areas of the absorbent article are joined together by means of embossing and/or ultrasonic processing. In this way a product with simple structure can be provided.

The absorbent core may have two longitudinal sides and wherein the topsheet and backsheet can extend in transverse direction of the article outside the longitudinal sides of the core and wherein at least the backsheet is further prolonged in the transverse direction of the article to create at least one flap extending along any of the longitudinal sides of the core, the flap being provided with pressure sensitive adhesive affixed to the garment facing surface of the backsheet. The flaps improve the leakage control of the product while secure attachment of the product can be provided.

In one embodiment also the topsheet is further prolonged in the transverse direction of the article to create at least one flap extending along any of the longitudinal sides of the core, the topsheet and the backsheet forming a laminate in the flap. Thus, robust flaps or wings may be provided.

Preferably, less than 15% of tested products exhibit apertures/tears in the backsheet when tested according to a modified standard release force-method described in the description. The apertures/tears may exhibit in any area of the product such as wings or in the area of the core region. Absorbent articles having damages in this low degree provide sufficient strength.

Suitably, the backsheet is a polyolefin-based casted film. Casted films are commonly used as backsheet materials.

The breathable polyolefin-based film of the backsheet has a grammage of from 15-25 gsm, preferably from 18-22 gsm and most preferably from 19-21 gsm. Such grammage provides for good handleability during manufacturing. By virtue of having the grammage within the mentioned interval, material costs can be kept low while a desired tear resistance measured according to Elmendorf Tear ASTM D1922 (15) can be provided.

The pressure sensitive adhesive is preferably a pressure sensitive hot-melt adhesive which is spray-coated or slot-coated to the garment facing surface of the backsheet to form at least one adhesive string which covers from 5-90% of the total surface of the backsheet. Thus, sufficient attachment to the garment can be provided for most fabrics. The at least one adhesive string may cover for example 20-90%, or 30-80% or 40-60% of the total surface of the backsheet. The adhesive may be applied to the backsheet in various patterns, such as for example spots, squares, single full or intermittent lines or multiple full or intermittent lines, which may be parallel or not. Other patterns are also possible. It is desirable to keep the coverage as low as possible to keep the costs as low as possible. Also by keeping the coverage as low as possible, the breathability of the product is affected as little as possible. For example, the backsheet may be provided with regions that are spray coated and regions that are slot coated. The backsheet may comprise a spray-coated adhesive on a surface to be attached on a body facing surface of a crotch region of a garment and a slot-coated adhesive on a surface to be attached on an outer surface of the crotch region of the garment. Thus, improved attachment can be provided.

The pressure sensitive adhesive may be spray-coated or slot-coated to the garment facing surface of the backsheet to form at least two adhesive strings that cover from 10-95% of the total surface of the backsheet. Thus, further improved attachment can be provided, also for fabrics containing synthetic fibres. The at least two adhesive strings may cover for example 20-90%, or 30-80% or 40-60% of the total surface of the backsheet.

The surface weight of the adhesive disposed on the backsheet can be between 15 and 40 $g/m^2$. By providing the adhesive with this range, it is possible to keep the costs as low as possible, while satisfactory attachment can be provided with the different application methods, i.e. spray coating and slot coating.

The backsheet film may lye striped with lighter and darker fields next to each other. The stripes can extend in the direction of the longitudinal central line or the stripes can extend in the transverse direction of the article. In this way the appearance of the article can be controlled and the strength of the backsheet material may be affected.

The film may comprise inorganic filler, preferably calcium carbonate, from 20 to 60 percent by volume of the polyolefin/filler composition. The filler provides breathability to the film in a well-controlled way.

Further features and advantages are described more in detail in the detailed description with reference to the appended drawings.

BRIEF DESCRIPTION OF THE DRAWINGS

Embodiments of the invention will be described in greater detail below with reference to the figures which are shown in the accompanying drawings.

DETAILED DESCRIPTION OF PARTICULAR EMBODIMENTS

Absorbent articles in the present disclosure are disposable personal hygiene articles aimed for absorbing body exudate, such as blood or urine, and by such absorbent articles are meant for example adult incontinence articles, sanitary towels and panty liners. The absorbent articles are releasably attachable on a garment, suitably an undergarment, of a user by means of adhesive. Absorbent article of the present disclosure comprises a liquid-permeable topsheet, a liquid-impermeable backsheet and a core placed between the topsheet and the backsheet. The topsheet has a body facing surface which is aimed to be in contact with skin of the user in the crotch area and thus face the user. The topsheet has also a garment facing surface which is on the opposite side of the topsheet and thus faces towards the garment of the user and therefore away from the user. The liquid-impermeable backsheet has also a body facing surface and a garment facing surface.

The absorbent article may have an essentially hourglass-shaped outer contour in the plane of a longitudinal and transverse extension of the absorbent article, but other shapes, such as asymmetrical shapes are also conceivable. The absorbent article may comprise at least one flap or "wing" that extends in transverse direction of the article outside the longitudinal sides of the core. Usually at least the backsheet is further prolonged in the transverse direction of the article to create the at least one flap extending along any of the longitudinal sides of the core. Usually there are two flaps on each side of the absorbent core. The at least one flap is provided with pressure sensitive adhesive affixed to the garment facing surface of the backsheet.

According to one variant, the absorbent core has a smaller extension in a plane of the longitudinal and transverse extension of the backsheet and/or topsheet. In this case the body facing surface of the backsheet is joined to the garment facing surface of the topsheet and the core is located inside the area where the backsheet is joined to the topsheet.

Alternatively, the backsheet and the topsheet have substantially the same extension in a plane of the longitudinal and transverse extension of the absorbent article. The topsheet can be joined together with the subjacent backsheet and the absorbent core, for example by means of adhesive, ultrasonic jointing or by means of some form of thermal bonding.

According to one embodiment the core, which has two longitudinal sides, and the topsheet and backsheet extend in transverse direction of the article outside the longitudinal sides of the core. At least the backsheet is further prolonged in the transverse direction of the article to create at least one flap extending along any of the longitudinal sides of the core. The flap is provided with pressure sensitive adhesive affixed to the garment facing surface of the backsheet. Alternatively, also the topsheet is further prolonged in the transverse direction of the article to create at least one flap extending along any of the longitudinal sides of the core, the topsheet and the backsheet forming a laminate in the flap. The flaps can then be used to be folded around the leg openings of the briefs, and thus provide an improved leakage protection and secure attachment to the garment of the user.

The absorbent article may comprise further layers, such as an admission layer, also called an acquisition layer, which is located beneath the topsheet. The acquisition layer is intended to quickly absorb liquid and disperse the liquid before it is transported to the absorbent core, where it is retained. The acquisition layer preferably comprises low density air-laid or wadding. The acquisition layer can be joined with the topsheet. The topsheet and the backsheet and the optional acquisition layer may be attached together by embossing or by means of ultrasonic processing to form a laminate. If the layers are attached together by means of ultrasonic processing, at least one of the topsheet, acquisition layer and the backsheet comprises a thermoplastic material. All the layers may be laminated together or only the topsheet and the acquisition layer are laminated together and the other layers are attached together by means of embossing or adhesive. When laminated together the layers are joined by means of a reinforcement executed with ultrasonic processing essentially along its peripheral edge that forms an edge seal of the laminate so that the risk of any leakage and spread of liquid via the peripheral edge is minimized or eliminated. The reinforcement can extend from the periphery and towards the inside of the product for a distance of about 2-6 mm.

Topsheet usually includes regenerated cellulose fibres, polyester or other synthetic polymer fibres, or films and is provided on the body-facing side of the absorbent article. The topsheet is provided for comfort and conformability and directing the fluid to the underlying absorbent element. The liquid-permeable topsheet is preferably manufactured from a material that exhibits characteristics such as dryness and softness during the time when the absorbent product is being worn, because this topsheet is in contact with the wearer's body. It is also desirable for the topsheet to have a soft and textile-like surface which remains dry, even in the event of repeated wetting. The topsheet can consist of a nonwoven material, for example, with a soft and smooth surface, such as a spunbond material made from polypropylene fibres. A perforated, hydrophobic nonwoven material may be used in order to permit the surface that is closest to the wearer's body to be kept dry, in conjunction with which openings are formed in the material that are larger than the holes between the fibres in the material. In this way, liquid can be led down through the perforated openings in the topsheet to the subjacent absorbent core. Other examples of materials for the topsheet are perforated plastic films such as a perforated polyester film attached to a nonwoven sheet (usually called laminate). The nonwoven part of the topsheet can also be a spunbond nonwoven material, an air-through nonwoven material, a spunlace nonwoven (hydroentangled) material, a meltblown nonwoven material, or a combination of these. The raw material can be polypropylene (PP), polyethylene (PE) polyester (PET), polyamide (PA), or a combination of these. If a combination is used, this can be a mixture of fibres from different polymers, although each fibre can also include different polymers (e.g. PP/PE bi-component fibres or PP/PE copolymers). Where appropriate, the plastic film can consist of PE or PP, PET, PLA or amyl (or, for that matter, any other thermoplastic polymer), or a mixture or copolymers of the aforementioned polymers. The topsheet is preferably a spunbond material comprising polypropylene fibres which provide for optimal comfort and handleability of the product. Other suitable fibres for making the nonwoven material are for example natural fibres such as bamboo, cotton and flax.

The absorbent core is appropriately manufactured from a suitable fibre material in the form of natural or synthetic fibres with absorbent characteristics, or a mixture or natural fibres and synthetic fibres or other absorbent materials of a previously disclosed kind that are suitable for use in, for example, sanitary towels, incontinence pads and panty liners. The absorbent core can also comprise a predetermined proportion, for example 10-30%, of superabsorbent material, that is to say polymer materials in the form of particles, fibres, flakes or the like, which possess the ability to absorb and chemically bind liquid equivalent to several times their own weight to form an aqueous gel. This imparts a very high liquid-absorbent capacity to the finished absorbent product while the product is still soft and easy to handle and manufacture.

The absorbent core can be of a unitary construction or it may comprise several layers of different materials. By "unitary construction" in the present context is meant that the absorbent core is constructed from essentially one type of material, this being essentially the same material, or essentially the same combination of two or more materials throughout the absorbent core. Variations in density and concentration of the material may occur, but these are limited to those which may be obtained without incorporation of regions which have been formed separately and then physically joined to each other. For example, when the absorbent core comprises a matrix of an absorbent material with absorbent characteristics, e.g. hydrophilic fibres, and superabsorbent material, the relative concentrations of superabsorbent material and fibres may be different in different parts of the core. The absorbent material could also be a hydrophobic material that has the capability to retain liquid within the structure of the material. However, when the construction is unitary, the absorbent core does not, for instance, comprise layers or laminates of different composition. Likewise, variations in the density or concentration of various components across the longitudinal direction, the transverse direction or the thickness direction of the absorbent core may occur.

Alternatively, the core may comprise areas or layers of different composition which are formed separately and later joined together, whereby the core is of "non-unitary construction". The aforementioned absorbent core can comprise one or several layers and it usually comprises a superabsorbent material. The absorbent core of non-unitary construction is typically built up by one or more layers of defibrillated cellulose fibres, for example cellulose fluff pulp. Other materials, which may be used, are for example absorbing or wettable nonwoven material, foam material, synthetic fibre materials or peat.

Super absorbent polymers (SAP), is material in the form of fibres, particles, granules, film or the like, which material has the ability to absorb fluid corresponding to several times the weight of the superabsorbent material. The superabsorbent material binds the fluid and forms a fluid-containing gel. Moreover, the absorbent core may comprise binders, form-stabilising components or the like. The absorbent core may be chemically or physically treated in order to change the absorption properties. The core may be compressed and it is also possible to enclose the absorbent layer(s) in an envelope of for example tissue material. Thus, the absorbent core can be arranged in several different ways as long as proper absorbent properties are achieved.

Typically, the absorbent core has in its longitudinal direction an outstretched form, and may for example be essentially rectangular, T-shaped or hourglass-shaped. An hourglass-shaped absorbent core is wider in the front and rear parts than in the crotch part, in order to provide an efficient fluid absorption simultaneously as the design facilitates the product to form and to close around the user, thereby giving a better fit around the legs. Also, the absorbent core can be designed in a more complex form, so that comfort, fitting, or absorption properties are optimised.

In the present disclosure, according to one embodiment, it is essential that the backsheet material or film is liquid-impermeable while it is breathable. In this way the film may improve the microclimate during use of the article by improving the handling of transpiration that comes continuously from the skin of the user by means of transporting the transpiration through the backsheet material. Otherwise, moisture would accumulate between the skin of the user and the absorbent article.

By liquid-impermeable backsheet film is meant that the film possesses high resistance to penetration by liquid. The backsheet film is arranged to prevent any leakage of excreted fluid from the absorbent product. The backsheet is also, on the other hand, executed so that it is vapour-permeable, i.e. breathable. The term "breathable" is used to describe a film which allows the passage of vapor. It typically comprises pores through which vapor can pass. Various methods for measuring the breathability of films have been developed. Breathability according to the present invention can be measured using NWSP 070.4.RO (15).

Polymer films which allow vapor to pass through them by virtue of their pores are known. It is also known to use so called breathable backsheets for absorbent articles, i. e. water vapor permeable backsheets that allows water vapor to be transported from within the absorbent article to the outside of the absorbent article via the backsheet, i. e. in the Z-direction. The breathable backsheets are intended to diminish the amount of water vapor within the article, since such water vapor may cause a too humid microclimate adjacent the skin of the user. Such humid microclimate may cause irritation on the user's skin.

The pores in such films can be introduced in a number of ways, including mechanical means or the application of heat or an electric discharge. For example, the backsheet can be manufactured from a liquid-impermeable material which comprises appropriately a thin and liquid-proof plastic film. For example, plastic films of polyolefin-based polymers, such as polyethylene and polypropylene are suitable. It is desirable that the film has a relatively low grammage of from 15-25 gsm, preferably from 18-22 gsm and most preferably from 19-21 gsm. The polyolefin-based film of the present disclosure is suitably polyethylene-based. By virtue of having the grammage within the mentioned interval, material costs can be kept low while a desired tear resistance measured according to Elmendorf Tear ASTM D1922 (15) can be provided. To render the backsheet breathable, the film is micro-perforated or comprises an inorganic filler material, such as calcium carbonate particles. The amount of the inorganic filler is suitably from 20 to 60 percent by volume of the polyolefin/filler composition. The higher the amount of inorganic filler, the weaker the mechanical strength of the film is. Therefore, there preferably must be a balance between the breathability and strength so that the film will not be damaged during the use or when the absorbent article is removed from a garment after the use.

Thus, pores can be introduced into polymer films by mixing particles of a brittle inorganic filler material in the polymer resin. A precursor film is formed from the resin, and then the precursor film is stretched, causing the particles of the filler material to break. This in turn creates fine pores in the film, which extend from one face of the film to the other, making it breathable. The fine pores in the breathable polymer film also discourage the passage of liquid, making such films suitable for backsheet materials where liquid-impermeable, yet breathable films are required. Methods for forming breathable films in this way are described inter alia in GB 2 068 968 and EP 0 779 325. The filler material may be an inorganic particulate filler material, such as calcium carbonate. When the film is stretched, cavities are formed around the particles. These cavities are large enough for a moisture in gaseous phase to be transported through the film, but too small for liquid to pass through. Therefore, such film materials are breathable, but liquid-impermeable but also weaker than unbreathable films that do not contain an inorganic particulate filler material. Furthermore, since there is a desire to decrease material costs, the grammage of the backsheet films is decreased and the films become brittle and can thus easily break. Therefore, there may be a risk that the absorbent article breaks, and pieces of the article will remain attached to the garment.

The breathability is measured according to the present invention by means of a Water Vapour Transmission Rate measured according to NWSP 070,4.RO (15). The value is at least 1000 g/m$^2$/24 h and preferably at least 3000 g/m$^2$/24 h. The breathability may be at least 7000 g/m$^2$/24 h, whereby an even more improved microclimate during the use of the absorbent article can be provided. The breathability can be up to 10000 g/m$^2$/24 h. With higher values than 10000 g/m$^2$/24 h there is a risk that the tear resistance of the article measured according to Elmendorf Tear ASTM D1922 (15) will become too low, and the problems stated above will appear. The tear resistance measured according to Elmendorf Tear ASTM D1922 (15) is at least 300 mN, preferably at least 500 mN. Normally, the upper limit is, or is about, 1200 mN. Tear resistances higher than that will affect the breathability negatively.

Furthermore, in the present disclosure, the backsheet film is striped with lighter and darker fields next to each other. By means of the stripes the aesthetical appearance of the article can be improved while the tear resistance is not negatively affected. The stripes may extend along the longitudinal direction of the article or the stripes extend along the transverse direction of the article. The stripes may be utilized when the article is used. For example, when the stripes extend along the longitudinal direction of the article, they can be used to facilitate the positioning of the article to the garment of the user.

Absorbent articles in the present disclosure comprise on the garment facing surface of the backsheet a pressure-sensitive adhesive, usually in the form of one or more lines or strings of adhesive applied to the surface. The adhesive is optionally protected by a release paper which has to be peeled away before the product is attached to the garment.

The adhesive material can be any of a large number of pressure sensitive adhesives that are commercially available, including cold pressure-sensitive adhesives such as the acrylate adhesives, generally combined with tackifiers such as polyterpenes, or rapid-setting thermoplastic adhesives (or hot-melt adhesives) such as styrene and butadiene copolymers. Other ingredients such as fillers, antioxidants and pigments may be included. The adhesive may also comprise a double faced adhesive tape or another type of adhesive. The adhesive may be applied to the backsheet in various patterns, such as for example spots, squares, single full or intermittent lines or multiple full or intermittent lines, which may be parallel or not. Other patterns are also possible. Suitably, the pressure sensitive adhesive is a pressure sensitive hot-melt adhesive. The adhesive can be spray-coated or slot-coated to the garment facing surface of the backsheet. The pattern preferably forms at least one adhesive string. The pattern suitably covers from 5-90% of the total surface of the backsheet. The pattern may cover 20-90%, 30-80% or 40-60% of the total surface of the backsheet. The backsheet may comprise a spray-coated adhesive on a surface to be attached on a body facing surface of a crotch region of a garment, or in another words, in the area below the absorbent core. A slot-coated adhesive may be provided on a surface to be attached on an outer surface of the crotch region of the garment. In this way, secure attachment can be provided while the application process of the adhesive can be easily controlled. The pressure sensitive adhesive can alternatively be spray-coated or slot-coated to the garment facing surface of the backsheet to form at least two adhesive strings that cover from 10-95% of the total surface of the backsheet. In this way, secure attachment can be provided. The pattern may cover 20-90%, 30-80% or 40-60% of the total surface of the backsheet. Suitably the surface weight of the adhesive disposed on the backsheet is between 15 and 40 g/m$^2$.

The disposable hygiene article may comprise a release liner releasably fastened to a garment facing side of the article by means of an adhesive and wherein the release liner is fastened to the inner surface of the elongated sheet by means of adhesive. The release liner protects the adhesive regions on the garment-facing side of the hygiene article while it also provides for a more robust structure for the article before use.

The absorbent article of the present disclosure is suitably adapted for use with a garment comprising fine fabrics. Fine fabrics may comprise synthetic fibres, also referred to as micro-fibres or for example silk. The garment may thus comprise a synthetic fabric. Synthetic fibres usually have less than 1 denier and a diameter in cross section of less than 10 μm. Synthetic fibres are used to form fabrics having good mechanical performance, while the fabrics are thin and have very good strength, uniformity and processing characteristics. The fabrics are often also soft and provide good breathability. Examples of synthetic fibres are nylon, polyester, acrylic, spandex, rayon and modal, but are not limited to these.

Examples of articles in which the backsheet material, which is a breathable polyolefin-based film and has a Water Vapour Transmission Rate measured according to NWSP 070.4.RO (15) of at least 1000 g/m$^2$/24 h, preferably at least 3000 g/m$^2$/24 h, and a tear resistance measured according to Elmendorf Tear ASTM D1922 (15) of at least 300 mN, can be used are shown in the attached drawings and explained in further detail below.

Figure 1:
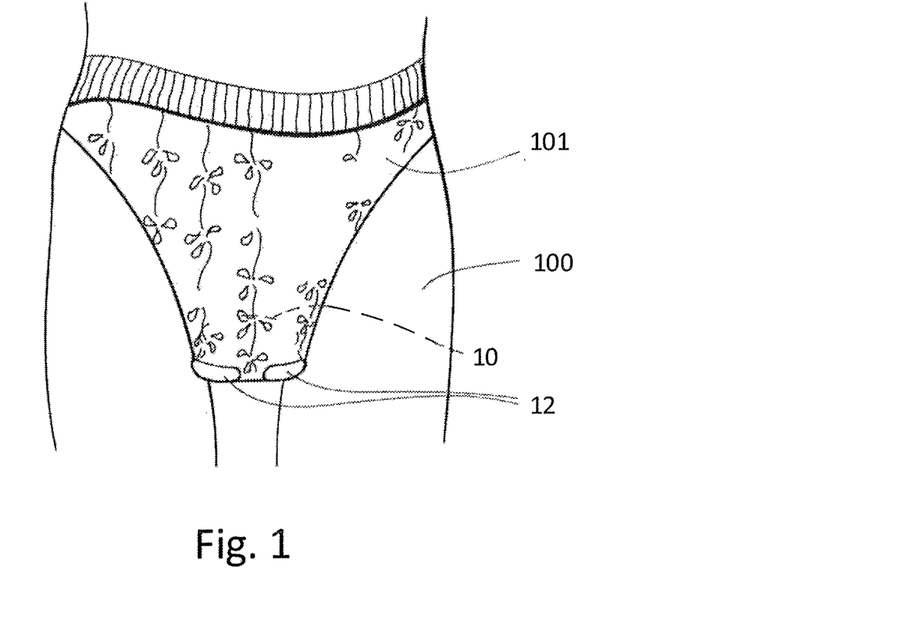
FIG. 1 shows a wearer from the front wearing a sanitary towel provided with side flaps inside a pair of briefs.
Figure 2:
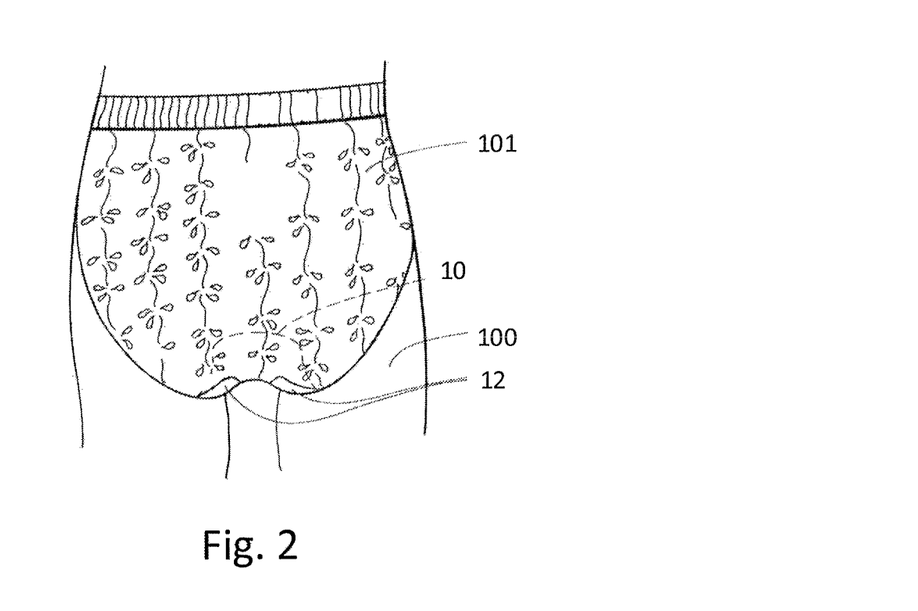
FIG. 2 shows a wearer from the rear wearing the sanitary towel provided with side flaps inside a pair of briefs.

FIGS. 1 and 2 show a wearer 100 seen from the front and, respectively, from the rear, wearing a sanitary towel 10 inside a pair of briefs 101. The sanitary towel has been designed with side flaps 12 which have been folded around the edges of the briefs in the crotch region.

Figure 3:
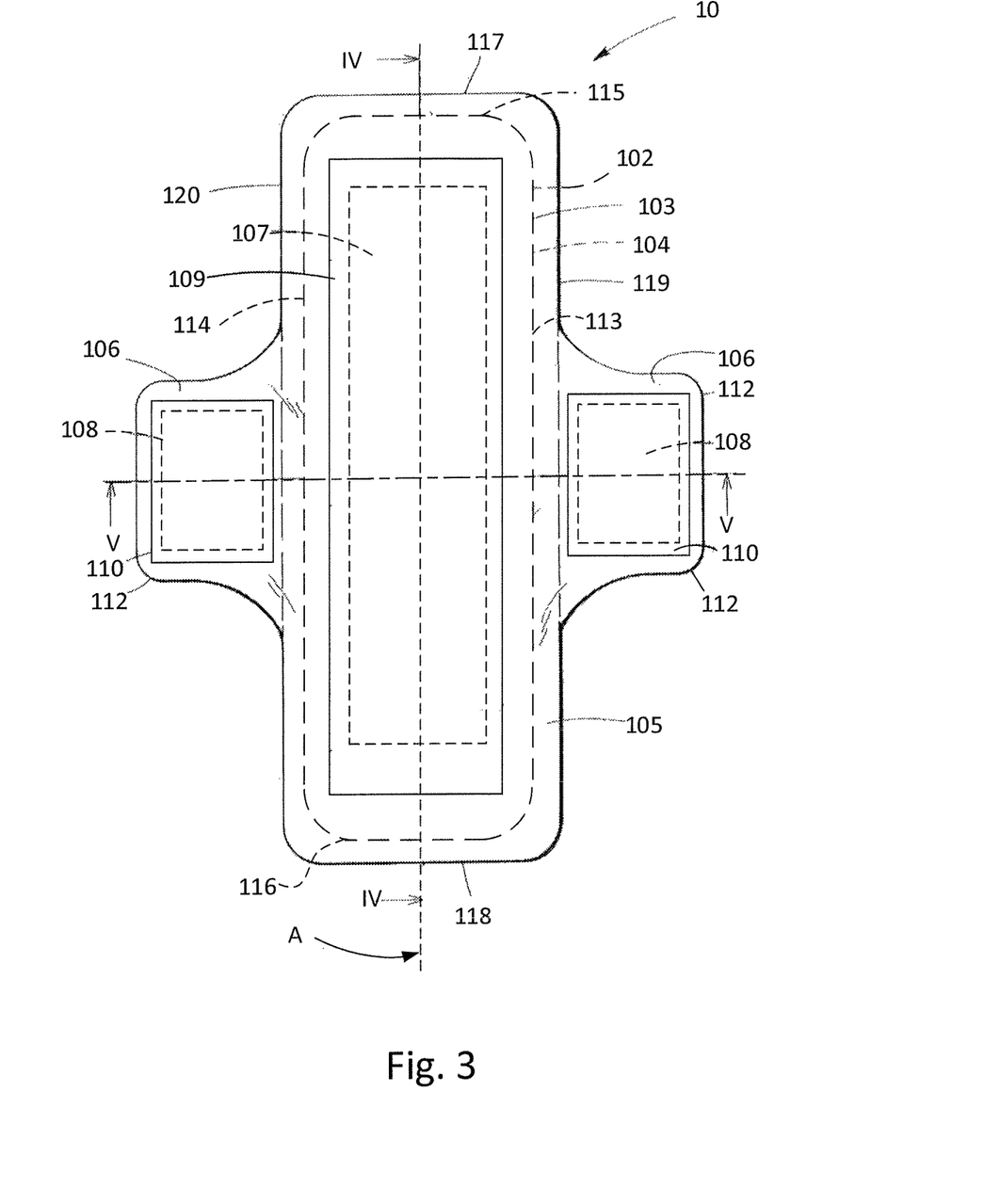
FIG. 3 shows a sanitary towel, seen from a garment facing side which is to face the briefs during use.
Figure 4A:
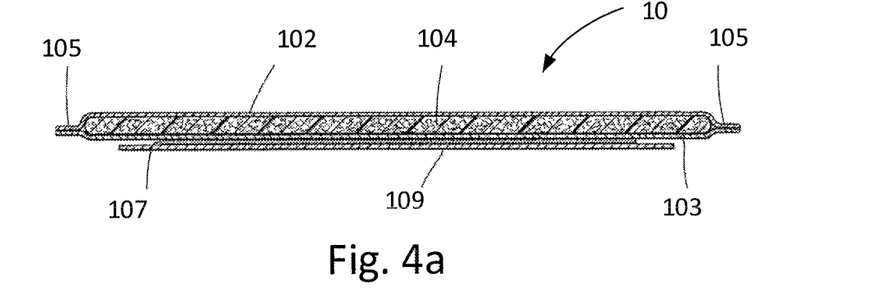
FIG. 4a shows a section along the line IV-IV through the sanitary towel in FIG. 3. However, the towel is shown the body facing side upwards such that the topsheet faces upwards and the backsheet faces downwards.
Figure 4B:
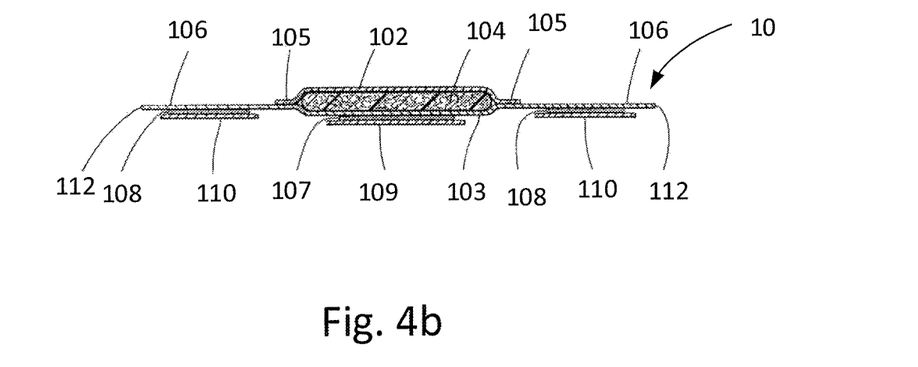
FIG. 4b shows an embodiment of a section along the line V-V through the towel in FIG. 3. However, the towel is shown the body facing side upwards such that the topsheet faces upwards the backsheet faces downwards.
Figure 4C:
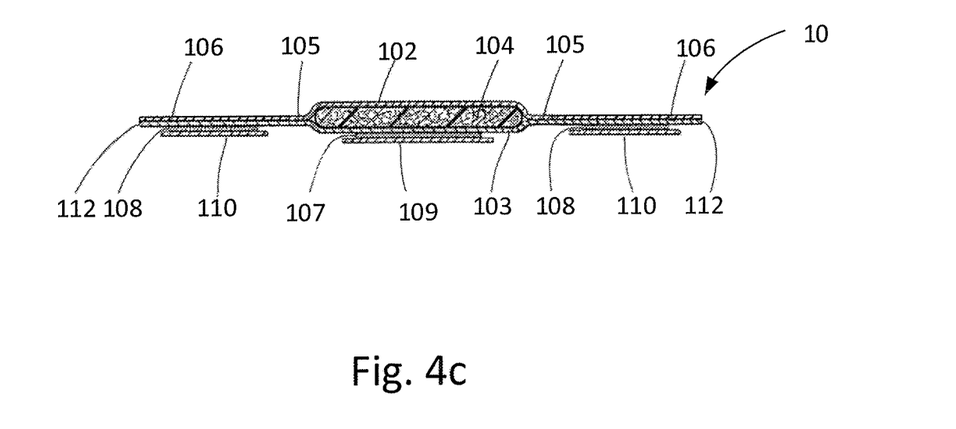
FIG. 4c shows another embodiment of a section along the line V-V through the towel in FIG. 3. However, the towel is shown the body facing side upwards such that the topsheet faces upwards the backsheet faces downwards.

FIG. 3 shows the sanitary towel 10 seen from the side which is intended to face the underwear of the wearer during use. The sanitary towel 10 has a longitudinal central line (A) extending through the absorbent article and two transverse end edges 117, 118 extending perpendicular to the central line (A) and two longitudinal side edges 119, 120 extending in the direction of the central line (A). FIGS. 4a, 4b and 4c show cross sections through the sanitary towel in FIG. 3 in two alternative embodiments. However, the cross sections are seen from the side facing the wearer during use, i.e. the sanitary towel is shown such that a topsheet faces upwards and a backsheet faces downwards. The liquid-permeable topsheet 102 is arranged on that side of the sanitary towel 10 which is intended to face the wearer. The liquid-permeable topsheet 102 suitably consists of a soft, skin-friendly material as described above.

The sanitary towel 10 also comprises a liquid-impermeable backsheet 103 arranged on that side of the sanitary towel which is to face away from the wearer. The backsheet material is of the type explained above and has a Water Vapour Transmission Rate measured according to NWSP 070.4.RO (15) of at least 1000 g/m$^2$/24 h, preferably at least 3000 g/m$^2$/24 h, and a tear resistance measured according to Elmendorf Tear ASTM D1922 (15) of at least 300 mN. Positioned between the liquid-permeable topsheet 102 and the liquid-impermeable backsheet 103 is an absorbent core 104 which can comprise one or more material layers. The core 104 may have an essentially rectangular shape or it may have another, e.g. asymmetrical shape. Suitable materials and structures for the absorbent core have been explained above. The core 104 has two longitudinal sides 113, 114, respectively, and two transverse sides 115, 116 respectively. The two layers, the liquid-permeable topsheet 102 and the liquid-impermeable backsheet 103, are interconnected and form a projecting edge connection 105 around the longitudinal side edges 119, 120 and the transverse end edges 117, 118 of the sanitary towel. The connection can be made by any known technique suitable for the purpose, such as gluing, welding or sewing. The sanitary towel also has two side flaps 106 arranged on either side of the absorbent core 104, the side flaps 106 projecting in the transverse direction from each longitudinal side edge 119, 120. The side flaps 106 are of such shape and size that, during use, they can be folded around the leg openings of the briefs. The side flaps 106 may be constituted by the liquid-impermeable backsheet 103 as illustrated in FIG. 4b. Alternatively, the side flaps 106 may be constituted by the liquid-impermeable backsheet 103 and the liquid-permeable topsheet 102 as illustrated in FIG. 4c.

An adhesive fastening means 107 is arranged on that surface of the liquid-impermeable backsheet 103 facing away from the wearer, in the area of the absorbent core 104. In this embodiment, the fastening means 107 is a pressure sensitive adhesive area arranged as a rectangle having a longer extension in the direction of the longitudinal central line (A) of the article than in the transverse direction. The adhesive area is protected by a removable protective layer 109, also referred to as a release liner. The protective layer 109 is intended to protect the adhesive fastening means 107 from dirt and dust and to prevent the glue from adhering in an undesirable manner to other surfaces or to itself until the sanitary towel is to be used. The projecting side flaps 106 have also been provided with fastening means 108 on the surface facing away from the wearer in order to ensure that the side flaps 106 make good contact against the outside of the briefs during use. The fastening means 108 is suitably constituted by a pressure sensitive adhesive in the form of an adhesive string which is protected by removable protective layers 110. The flaps 106 have an end edge portion 112 on respective side of the sanitary towel 10.

Figure 5:
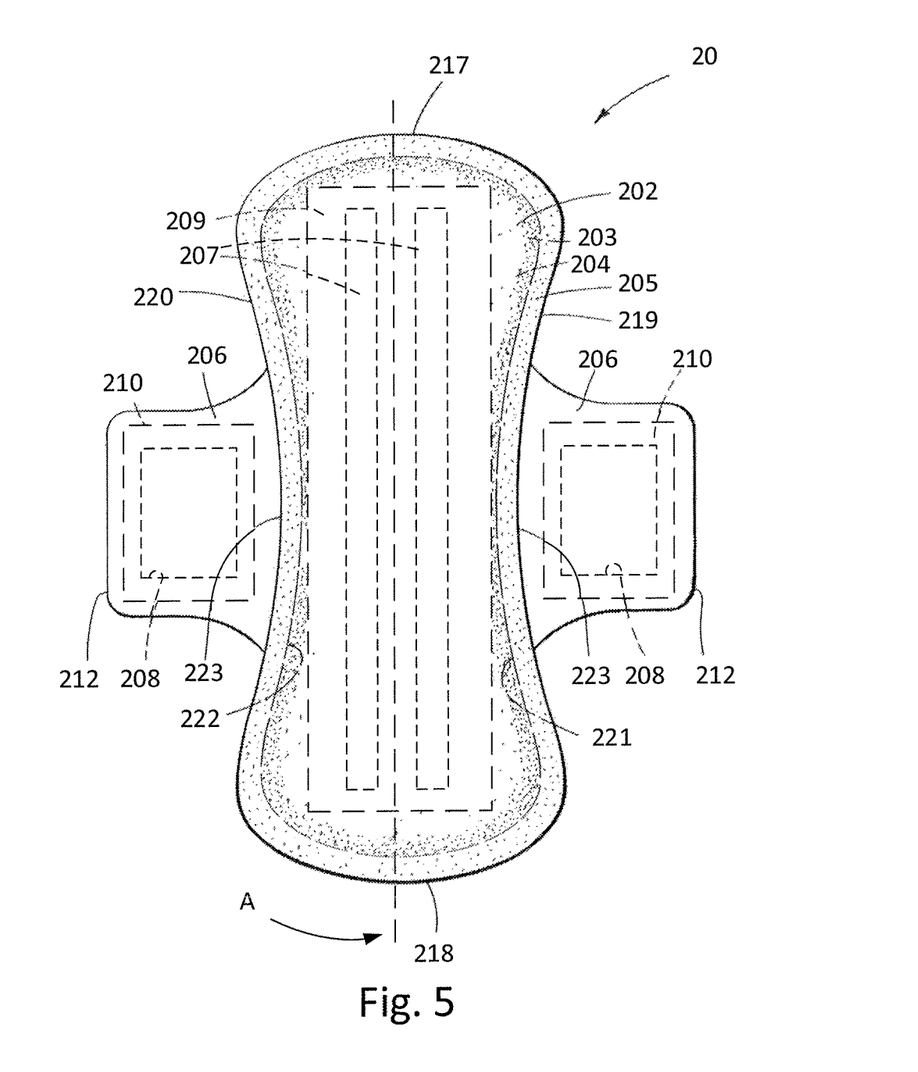
FIG. 5 shows a sanitary towel with an hourglass-shaped absorbent core comprising adhesive strings on the garment facing surface of the backsheet, seen from the side which is to face the wearer during use, i.e. the body facing side upwards.

FIG. 5 shows a sanitary towel 20 seen from the side which is to face the wearer during use. The sanitary towel 20 is of fundamentally the same construction as the sanitary towel 10 illustrated in previous figures. The numbering of the different parts of the sanitary towel in FIG. 5 is therefore by analogy with that used in the description of the sanitary towel 10 in the previous figures. However, the sanitary towel 20 shown in FIG. 5 differs in two respects from the sanitary towel 10 described previously, firstly in that the sanitary towel 20 has an hourglass-shaped absorbent core 204. Secondly, the adhesive area comprises two adhesive strings 207 below the core on the backsheet 203. By giving the absorbent core 204 an hourglass shape, the sanitary towel can be afforded better contact against the thighs of the wearer and thus improved comfort during use of the sanitary towel 20. The sanitary towel 20 has also been designed with a liquid-permeable topsheet 202 which has a shape which follows the contour of the longitudinal sides or edges 221, 222 of the absorbent core at least in the area of a crotch portion 223. By designing the liquid-permeable topsheet 202 so that it follows the longitudinal sides or edges 221, 222 of the absorbent core, an aesthetically improved sanitary towel is obtained.

In the similar way as in the embodiment shown in FIG. 3-4b a liquid-permeable topsheet 202 is arranged on that side of the sanitary towel which is intended to face the wearer. The sanitary towel 20 also comprises a liquid-impermeable backsheet 103 arranged on that side of the sanitary towel which is to face away from the wearer. The backsheet material is of the type explained above and has a Water Vapour Transmission Rate measured according to NWSP 070.4.RO (15) of at least 1000 g/m$^2$/24 h, preferably at least 3000 g/m$^2$/24 h, and a tear resistance measured according to Elmendorf Tear ASTM D1922 (15) of at least 300 mN. Positioned between the liquid-permeable topsheet 202 and the liquid-impermeable backsheet 203 is an absorbent core 204 which can comprise one or more material layers. The two layers, the liquid-permeable topsheet 202 and the liquid-impermeable backsheet 203, are interconnected and form a projecting edge connection 205 around the longitudinal side edges 219, 220 and the transverse end edges 217, 218 of the sanitary towel. The sanitary towel also has two side flaps 206 arranged on either side of the absorbent core 204, the side flaps 206 projecting in the transverse direction from each longitudinal side edge 219, 220. The side flaps 206 are of such shape and size that, during use, they can be folded around the leg openings of the briefs. The side flaps 206 may be constituted by the liquid-impermeable backsheet or by the liquid-impermeable backsheet 103 and the liquid-permeable topsheet 102.

An adhesive fastening means 207 is arranged on that surface of the liquid-impermeable backsheet 203 facing away from the wearer, in the area of the absorbent core 204. The adhesive means comprises two adhesive strings. In this embodiment, the fastening means 207 is comprised of two pressure sensitive adhesive strings or rectangles having a longer extension in the direction of the longitudinal central line (A) of the article than in the transverse direction. The adhesive area is protected by a removable protective layer 209, also referred to as a release liner. The projecting side flaps 206 have also been provided with fastening means 208 on the surface facing away from the wearer in order to ensure that the side flaps 206 make good contact against the outside of the briefs during use. The fastening means 208 is suitably constituted by a pressure sensitive adhesive in the form of an adhesive string which is protected by removable protective layers 210. The flaps 206 have an end edge portion 212 on respective side of the sanitary towel 20.

Figure 6:
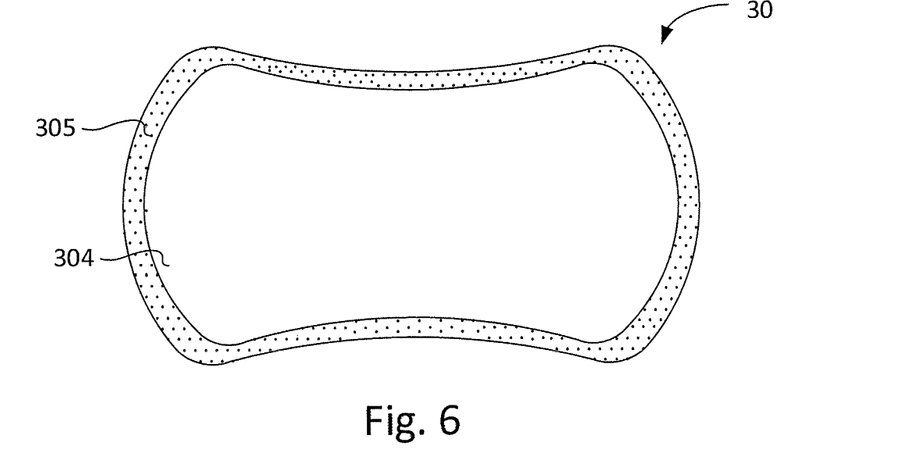
FIG. 6 shows a panty liner with an hourglass-shaped topsheet, absorbent core and backsheet.
Figure 7:
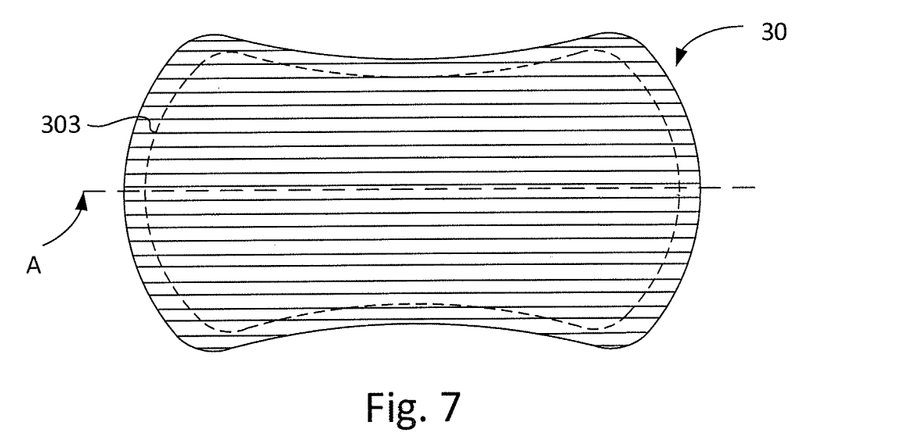
FIG. 7 shows the panty liner of FIG. 6 with a backsheet material having stripes extending along the longitudinal direction of the article.
Figure 8:
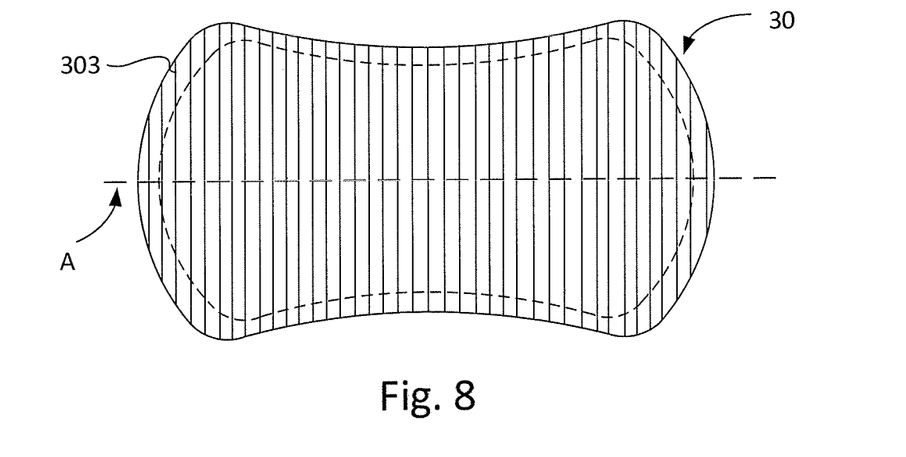
FIG. 8 shows the panty liner of FIG. 6 with a backsheet material having stripes extending along the transverse direction of the article.

In FIG. 6 a panty liner 30 is shown from the user facing side. In this embodiment the absorbent core 304, the backsheet 303 (shown in FIGS. 7 and 8) and the topsheet (not shown) have substantially the same extension in a plane of the longitudinal and transverse extension of the absorbent article 30. The edge areas 305 of the absorbent article are joined together by means of embossing and/or ultrasonic processing. In FIG. 7 one embodiment of the backsheet material 303 is shown. In this embodiment the backsheet film 303 is striped with lighter and darker fields next to each other and the stripes extend in the direction of the longitudinal central line (A). In FIG. 8 the stripes extend in the transverse direction of the article (30).

Examples

The following measurement methods were used.

Method Description—Release Force of Product and Evaluation of Number of Damaged Products Aim and Samples The aim of the test method is to simulate what happens when the user removes an absorbent hygiene article from a panty and count how many absorbent articles are destroyed. It also aims to determine maximum strength between a product and polyester fabric. This is done by using a tensile tester, wherein the test is performed in a lengthwise direction. It should pull long enough to cover the whole length of a glued area. The tensile tester has a fixed bottom clamp and a moveable upper clamp. A suitable test apparatus and software are available from, for example, Zwick/Roell or Instron Corporation.

Apparatus and Settings

Zwick/Roell Model Z1.0

The pulling speed should be 500 mm/min;

The pulling length should be adapted to the glue string to be tested;

The distance between the clamps should be 50 mm;

The width of the clamps should be ≥100 mm;

Angle of test—180°;

Extra Tools Required

A weight of 2724 g, dimensions L 200 mm, W 61 mm, H 28 mm, warmed up to 40° c. (exerting a pressure of 22.7 g/cm$^2$ when put with the large side down);

Heating oven 40° C.;

Rolling weight apparatus, roll weight 600 g exerting a force of 1 N/cm, 1500 mm/min Scissor or punching tool, 50×200 mm;

Polyester fabric—Feininterock 100% PES, 75 g/m$^2$. The fabric was washed in a washing machine with centrifugation without a washing detergent at 40° C., 3 times. Subsequently, the fabric was dried at a room temperature of 23±1° C. and 50±5% r.h. for 10 hours.

Sample Preparation

Cut fabric by scissors or punching tool into pieces. The dimensions of the pieces are chosen such that it corresponds to the dimensions of the adhesive-covered area of the product. It should be cut in the longitude direction of the fabric.

Mark front of product—this is the part which should be placed in the upper clamp of tensile tester when performing the test later.

Remove protective covers from the product.

Lay down the product onto a table.

Lay down the fabric onto the back of an absorbent article. The fabric should cover the adhesive-coated area in the core region of the product.

The wings are folded and applied on the other side of the fabric.

Place fabric and the absorbent article into a rolling weight apparatus with fabric facing upwards and let it roll forth and back once.

Put samples in a heating oven (T=40° C.) in piles of maximum two samples on top of each other. Four hours in heating oven simulates wearing condition.

Load each pile with a weight and make sure it completely covers the adhesive coated area of the product Take out the samples after four hours and let them acclimatize one hour in 23±1° C. and 50±5% r.h.

Test Procedure

Attach the fabric in lower clamp and front of product in upper clamp of tensile tester. Sample shall be fastened straight and gently stretched (force before start of the test should not exceed 0.1 N).

Start the tensile tester. It should pull long enough to cover whole length of adhesive covered area. Note maximum force in N and make a visual assessment of the backsheet to see if any damage has occurred.

Results

The result should be a mean value of 20 measurements.

Maximum force of the peeling strength using one decimal (N)

Quantity of products with damaged backsheet is reported (%).

By damage is meant that there is a visible tear or aperture in the backsheet or that a portion of the backsheet has got stuck on the fabric.

Method Description—Tear Resistance in Backsheet Material

Aim and Samples

Tear resistance is measured according to Elmendorf Tear ASTM D 1922 (15). The aim of the test method is to determine the tear resistance of a backsheet material in whichever is the weakest direction, MD or CD. A test piece of the backsheet material is taken from the backsheet material as such and not from a produced absorbent article. Tear resistance is defined as the maximum force (mN) which is measured when the tearing of the test material occurs when the pendulum tear the material at a specified angle. The work required for the demolition of the test piece is measured as the decrease in potential energy when a pendulum is used to tear the material and measured by the loss of energy of the pendulum. A suitable test apparatus and software are available from, for example, Pro Tear Elmendorf-Tear Tester.

Apparatus and Settings

Pro Tear Elmendorf—Tear Tester

Pendulum—size 1600

Scissor or punching tool, dimensions see picture

Sample Preparation

Figure 9:
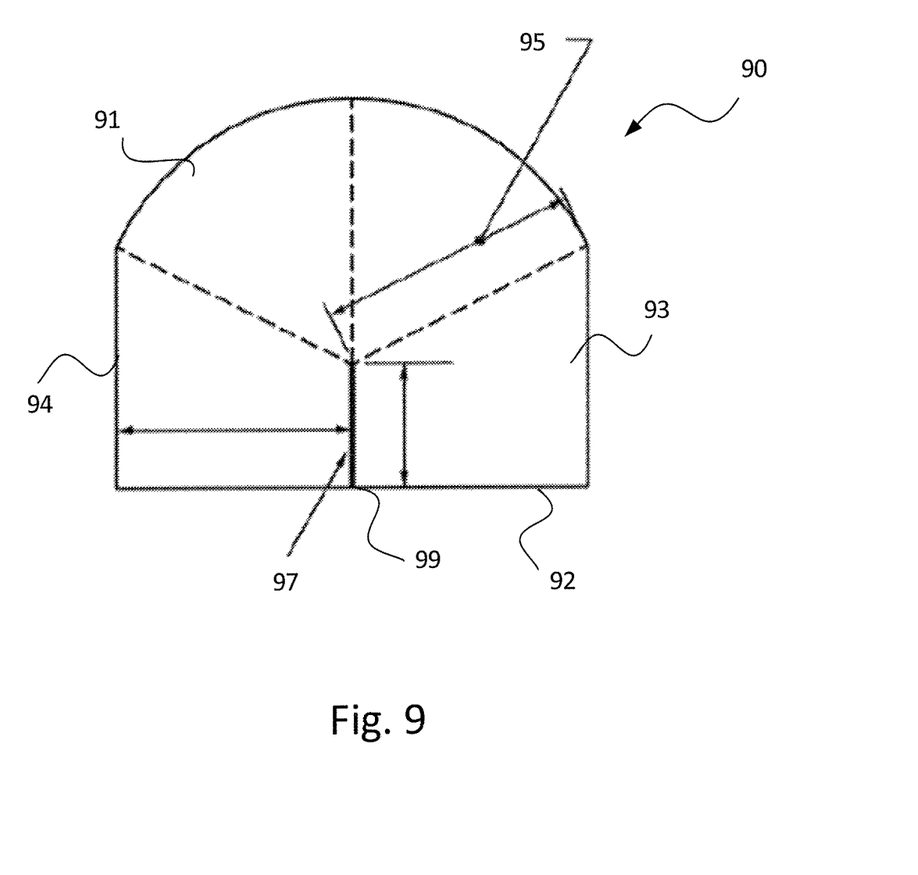
FIG. 9 shows test equipment for punching a test piece used in the method for measuring tear resistance Elmendorf Tear ASTM D1922.

Pieces of the backsheet test material are punched or cut out according to FIG. 9. The test piece 90 has a substantially rectangular bottom portion 93 and a semi-circular top portion 91. The bottom portion 93 comprises a slit 97, which is pre-cut or applied in the instrument, extending towards the top portion 91 and has a length 20 mm in a direction perpendicular to the extension of a bottom edge 92. The tear extends from a center point 99 of the bottom edge 92 of the test piece 90. The center point 99 is located at a distance of 38 mm from a side wall 94 of the rectangular bottom portion 93. The radius 95 of a tear is illustrated by reference number 95 and has a length of 43 mm.

Test Procedure

Attach sample between the two clamps. Pre-cut the test piece of the backsheet material. Start the pendulum and let it swing freely at least once. Stop the pendulum manually when there has been a break on the sample.

Results

The tear resistance shall be reported in mN.

Method Description—Breathability of the Backsheet Material

Aim and Samples

The aim of the test method is to determine the rate of water vapor transmission through a backsheet material.

Water Vapor Transmission Rate is measured according to EDANA/INDA Worldwide Strategic Partners Method NWSP 070.4.R.0 (15).

Apparatus and Settings

Water Vapor Transmission Rate is measured according to NWSP 070.4.R.0 (15) using a MOCON PERMATRAN-W Model 101K.

Sample Preparation

Backsheet samples were prepared according to NWSP070.4.R.0 (15) standard test.

Test Procedure

The test method was run as per the NWSP070.4.R.0 (15) standard test.

Results

The breathability shall be reported in g/m$^2$/24 h.

Summary of the Test Results

Table 1 below lists five different backsheet materials A, B, C, D and E, which were tested. Materials A, B and D are prior art breathable backsheet materials and material C is the breathable backsheet material according to the present disclosure. Material E is a non-breathable backsheet material.

TABLE 1

| Backsheet | Material code | Production technology (cast/blown) | Breathable/ non-breathable | Basis weight (g/m$^2$) |
|---|---|---|---|---|
| A | D21H | cast | breathable | 21 |
| B | D25H | cast | breathable | 25 |
| C | Sof-flex D20H | cast | breathable | 20 |
| D | Hycare H25 | blown | breathable | 24 |
| E | ME1197 | cast | non-breathable | 21 |

Table 2 below shows values for tear resistance measured according to Elmendorf Tear ASTM D 1922 (15) and breathability measured according to NWSP 070.4.RO (15) for the different backsheet materials A-E. It can be seen that the more breathable the backsheet material is, the lower the tear resistance of the material is (Sample D). On the other hand, when the backsheet material is not breathable, it can obtain very high tear resistance (material E). The backsheet material according to the present disclosure (material C) has a very good breathability while it has a higher tear resistance compared to the prior art backsheet materials A, B and D.

TABLE 2

| Backsheet | Tear resistance (mN) | WVTR (g/m$^2$/24 h) |
|---|---|---|
| A | 213 | 7600 |
| B | 239 | 7600 |
| C | 408 | 6000 |
| D | 181 | 11000 |
| E | 1120 | 0 |

Table 3 below shows the amount of articles with damaged backsheet and the release force to remove the article from the text fabric when tested according to the method "release force of product" described above. Absorbent articles having a similar structure as shown in FIG. 5 were tested. Each of the articles comprised adhesive strings 207 which had a width in the transverse direction of the article of 18 mm each. There was a distance of 12 mm between the strings 207. The length of the strings was 190 mm in the direction of the longitudinal center line A. Each of the strings 207 was slot-coated with a pressure sensitive hot-melt adhesive and the adhesive was applied in an amount of 26 g/m$^2$. The wings 206 were provided with a pressure sensitive hot-melt adhesive applied as a rectangle 208 having a length of 40 mm in the direction of the longitudinal center line A and a width of 13 mm in the transverse direction. Each of the rectangles 208 was slot coated and the adhesive was applied in an amount of 30 g/m$^2$. The article was commercially called "Libresse Ultra Normal with wings", and the grammage of the topsheet was 18 gsm, the acquisition material was an air-laid nonwoven with a grammage of 70 gsm, the core contained pulp-material at a grammage of 255 gsm and a superabsorbent material (SAP) at a grammage of 45 gsm. It can be seen that the force for the release is similar between the different backsheet materials but the number of indicated articles with damaged backsheet differs with the different backsheet materials. It can be seen that considerably fewer articles with damaged backsheet material are obtained by the use of the backsheet material according to the present disclosure (Article 1 with the backsheet material C) than with the prior art article (Article 2) with a breathable backsheet material D. The articles with non-breathable backsheet materials were not damaged in the test.

TABLE 3

| Article | Backsheet | Articles with damaged backsheet, (%) | Release force (N) |
|---|---|---|---|
| 1 | C | 15% | 16.1 |
| 2 | D | 80% | 15.9 |
| 3 | E | 0% | 15.5 |

Also, further tests were performed in which 350 respondents tested in a comparative test a product Libresse Ultra Normal. One article was provided with a non-breathable backsheet material as in Article 3 (backsheet E) in table 3 above and the other article was provided with a high breathable backsheet material which also had a high tear strength as in Article 1 (backsheet C) in table 3 above. The respondents found these products equal when it comes to not breaking and not leaving adhesive residue left in the panty.

Thus, it can be concluded that the backsheet material C according to the present disclosure provides good breathability while the strength of the material is improved compared to prior art backsheet materials, and thus a satisfactory relation between the breathability and strength is obtained.

The invention is not to be considered as being limited by the illustrative embodiments described here. All possible combinations and variants of the illustrative embodiments described are also intended to be included within the scope of the invention defined in the appended claims.

The invention claimed is:

1. An absorbent article comprising a liquid-permeable topsheet having a body facing surface and a garment facing surface, a liquid-impermeable backsheet having a body facing surface and a garment facing surface, wherein an absorbent core is positioned between the topsheet and the backsheet, and wherein the absorbent article has a longitudinal central line (A) extending through the absorbent article and wherein the absorbent article extends in the direction of the longitudinal central line (A) and a transverse direction, which is perpendicular to the direction of the longitudinal central line (A), and the absorbent article further comprises pressure sensitive adhesive on the garment facing surface of the backsheet, and wherein the backsheet is a breathable polyolefin-based film having a grammage of from 15-25 gsm, a Water Vapour Transmission Rate measured according to NWSP 070.4.RO (15) of at least 1000 g/m$^2$/24 h, and a tear resistance measured according to Elmendorf Tear ASTM D1922 (15) of at least 300 mN, wherein the pressure sensitive adhesive on the backsheet comprises a spray-coated adhesive on a surface to be attached on a body facing surface of a crotch region of a garment and a slot-coated adhesive on a surface to be attached on an outer surface of the crotch region of the garment.

2. The absorbent article according to claim 1, wherein the absorbent core has a smaller extension in a plane of the longitudinal and transverse extension of the backsheet and/or topsheet, and wherein the body facing surface of the backsheet is joined to the garment facing surface of the topsheet.

3. The absorbent article according to claim 1, wherein the absorbent core, the backsheet and the topsheet have substantially the same extension in a plane of the longitudinal and transverse extension of the absorbent article and wherein the edge areas of the absorbent article are joined together by means of embossing and/or ultrasonic processing.

4. The absorbent article according to claim 1, wherein the absorbent core has two longitudinal sides and wherein the topsheet and backsheet extend in transverse direction of the article outside the longitudinal sides of the core and wherein at least the backsheet is further prolonged in the transverse direction of the article to create at least one flap extending along any of the longitudinal sides of the core, the flap being provided with pressure sensitive adhesive affixed to the garment facing surface of the backsheet.

5. The absorbent article according to claim 4, wherein the topsheet is further prolonged in the transverse direction of the article to create at least one flap extending along any of the longitudinal sides of the core, the topsheet and the backsheet forming a laminate in the flap.

6. The absorbent article according to claim 1, wherein upon testing of a plurality of absorbent articles less than 15% of tested absorbent articles exhibit apertures and/or tears in the backsheet when tested according to a modified standard release force-method.

7. The absorbent article according to claim 1, wherein the backsheet is a polyolefin-based casted film.

8. The absorbent article according to claim 1, wherein the breathable polyolefin-based film of the backsheet has a grammage of from 18-22 gsm.

9. The absorbent article according to claim 1, wherein the pressure sensitive adhesive is a pressure sensitive hot-melt adhesive which is spray-coated or slot-coated to the garment facing surface of the backsheet to form at least one adhesive string which covers from 5-95% of the total surface of the backsheet.

10. The absorbent article according to claim 9, wherein the pressure sensitive adhesive is spray-coated or slot-coated to the garment facing surface of the backsheet to form at least two adhesive strings that cover from 10-95% of the total surface of the backsheet.

11. The absorbent article according to claim 1, wherein the surface weight of the adhesive disposed on the backsheet is between 15 and 40 $g/m^2$.

12. The absorbent article according to claim 1, wherein the backsheet film is striped with lighter and darker fields next to each other.

13. The absorbent article according to claim 12, wherein the stripes extend in the direction of the longitudinal central line (A) of the article.

14. The absorbent article according to claim 12, wherein the stripes extend in the transverse direction of the article.

15. The absorbent article according to claim 1, wherein the film comprises inorganic filler, preferably calcium carbonate, from 20 to 60 percent by volume of a polyolefin/filler composition defining the film.

16. The absorbent article according to claim 15, wherein the inorganic filler comprises calcium carbonate.

17. The absorbent article according to claim 1, the backsheet having a Water Vapour Transmission Rate measured according to NWSP 070.4.RO (15) of at least 3000 $g/m^2/24$ h.

18. The absorbent article according to claim 1, wherein the breathable polyolefin-based film of the backsheet has a grammage of from 19-21 gsm.

19. The absorbent article according to claim 1, wherein the backsheet has a tear resistance measured according to Elmendorf Tear ASTM D1922 (15) that is within a range of 300 mN to 1200 mN.

* * * * *